United States Patent [19]

Campbell et al.

[11] 3,962,040

[45] June 8, 1976

[54] METHOD AND APPARATUS FOR PLATING AND COUNTING AEROBIC BACTERIA

[75] Inventors: Jeptha E. Campbell; James E. Gilchrist, both of Cincinnati, Ohio

[73] Assignee: The United States of America as represented by the Department of Health, Education and Welfare, Washington, D.C.

[22] Filed: Jan. 28, 1975

[21] Appl. No.: 544,933

Related U.S. Application Data

[60] Division of Ser. No. 451,275, March 14, 1974, Pat. No. 3,892,632, which is a continuation-in-part of Ser. No. 149,137, June 2, 1972, Pat. No. 3,799,844.

[52] U.S. Cl. .............................................. 195/127
[51] Int. Cl.² ........................................... C12K 1/10
[58] Field of Search ..................................... 195/127

[56] References Cited
OTHER PUBLICATIONS

Gall et al., Developments in Industrial Microbiology; pp. 460–469 vol. 11; 1970.

*Primary Examiner*—A. Louis Monacell
*Assistant Examiner*—Robert J. Warden
*Attorney, Agent, or Firm*—Browdy and Neimark

[57] ABSTRACT

A method for determining the concentration of an unknown bacterial solution using only a single bacterial growth plate for the determination. The method comprises depositing a varying amount of bacterial solution on the surface of a solidified agar plate by continuously varying the amount of solution deposited in the shape of a spiral on the agar which is in a rotating Petri dish. Thus, a higher concentration of bacteria per unit length occurs at the center of the spiral and a decreasing concentration per unit length at the edge of the plate. The plate is then incubated and the colonies in a predetermined area of the plate are counted in order to determine the concentration of the unknown solution. The bacterial colonies in a predetermined area may be counted by interrupting a light or laser beam incident to a photodiode, the light being interrupted by the presence of a bacterial colony. The concentration of the unknown solution may then be determined by relating the number of colonies counted to the area on which they were deposited.

10 Claims, 6 Drawing Figures

U.S. Patent   June 8, 1976   Sheet 3 of 3   3,962,040
FIG.4
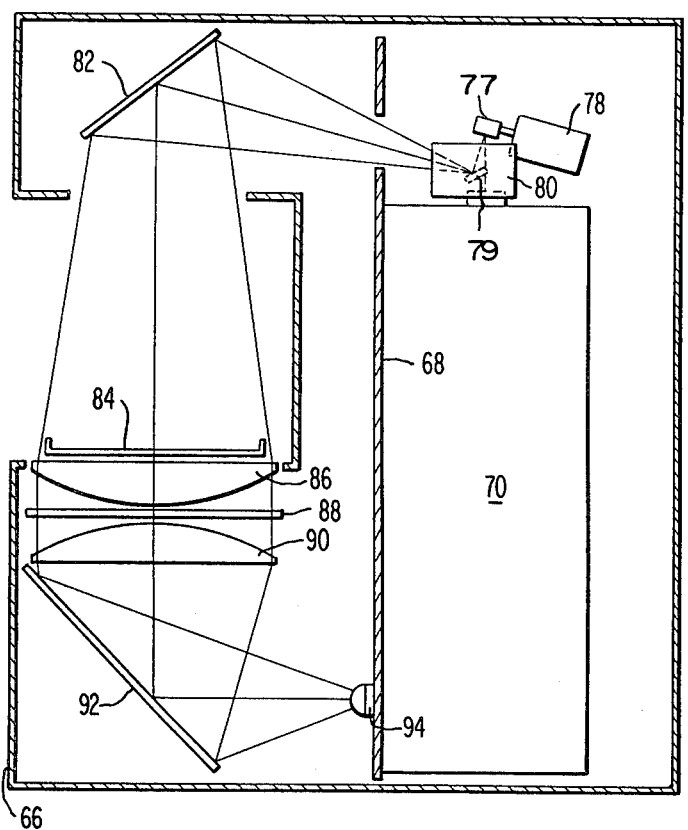
FIG.5
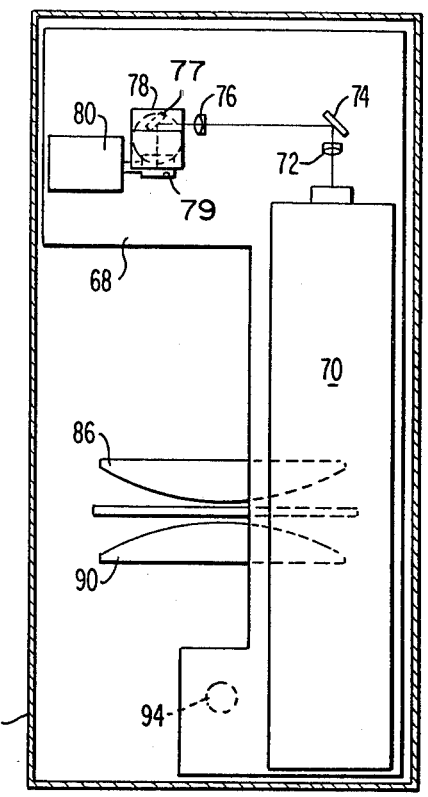
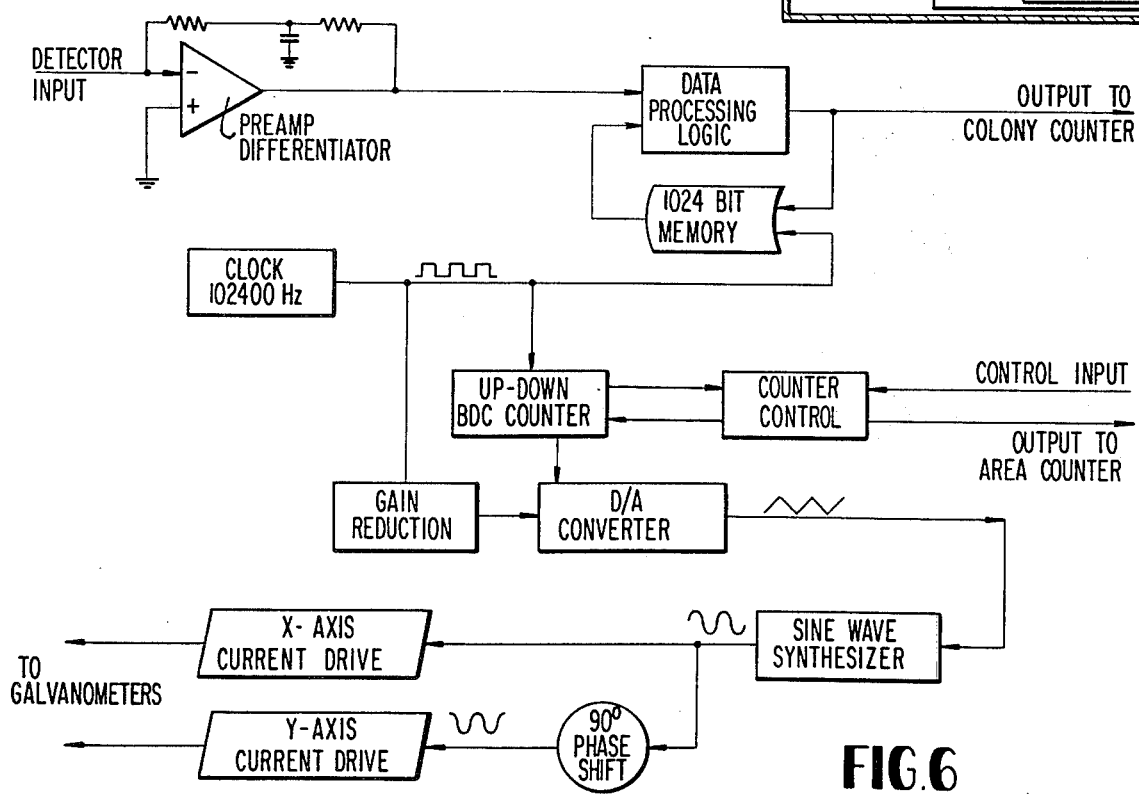
FIG.6

METHOD AND APPARATUS FOR PLATING AND COUNTING AEROBIC BACTERIA

CROSS REFERENCE TO RELATED APPLICATIONS

The present application is a division of application Ser. No. 451,275, filed Mar. 14, 1974, now U.S. Pat. No. 3,892,632, which in turn is a continuation-in-part of U.S application Ser. No. 149,137, filed June 2, 1972, now U.S. Pat. No. 3,799,844, which is hereby incorporated by reference.

FIELD OF THE INVENTION

The present invention relates to the quantifying of viable particles and, more particularly, to a method for depositing aerobic bacteria from a sample of unknown concentration on a solid culture medium in a variable amount followed by culturing and counting the colonies to determine the bacterial concentration of the original sample and to a device for automatically counting the bacterial colonies on a preselected portion of the medium.

BACKGROUND OF THE INVENTION

In the science of microbiology, which by its very definition is that branch of knowledge which concerns living micro-organisms, there is a never-ending need to observe, study, catalog and learn about bacteria, how they multiply, the size and operation of their colonies, their incubation periods, etc. There frequently arises, either in scientific microbiologic inquiries or in the field of medicine (e.g., for antibiotic sensitivity assay), the need to determine the total number of bacteria present in a sample, or the number of bacterial colonies which have incubated.

The normal procedure for determining the quantity of bacteria in an unknown solution, known as the pour plate method, is complex, involving making serial dilutions with multiple pipetting, and mixing each dilution with sterile liquid agar. A known aliquot of each dilution is mixed with an agar nutritive media in a Petri dish. This must all be done under sterile conditions to avoid the introduction of outside bacteria. The agar makes a gel and holds the bacteria in place. Upon incubation the bacteria reproduce sufficiently to form visible colonies which can be counted from one of the dilutions. The plates which contain too many or too few bacterial colonies are discarded and the one containing a countable number is visually counted. Knowing the number counted and the dilution from which the plate was made, the bacterial concentration in the original material may be calculated.

SUMMARY OF THE INVENTION

The present invention does not require the use of sterile pipettes, sterile dilution bottles, melted agar or multiple Petri dishes as does the prior art procedure. Thus, many of the weaknesses and shortcomings of the prior art are overcome. In the present invention the dilution is made by quickly and accurately depositing a small amount of the liquid of unknown concentration on the surface of one agar plate in a spiral of varying quantity. Preprepared agar plates, normally used only for qualifying procedures, are thereby useful for quantifying operations. Only one agar plate is needed, instead of many, and the preparation of the sample may be carried out in only about two minutes, some four or five times faster than the time required to prepare each sample by the conventional method using the serial dilutions.

The present invention is further capable of quickly and accurately determining aerobic bacteria present in a sample with a minimum of human error. A varying amount of solution is deposited on the surface of solidified agar plate in the configuration of an Archimedes spiral. The amount of solution being deposited on the agar is continuously decreasing, resulting in a higher concentration of bacteria per unit length at the center of the spiral and a decreasing concentration per unit length as the edge of the plate is approached. The plates are then incubated until the bacterial colonies become visible, the time necessary being dependent upon the bacterial species. standard By depositing solutions on the agar surface in the configuration of an Archimedes spiral and decreasing the amount of solution being deposited, the density of the bacteria and thus the density of the resultant colonies decreases from the center of the Petri dish toward the edge. Because the same volume is deposited in the same manner on each Petri dish, portions of the agar surface can be calibrated as to the amount of the solution deposited. Since the amount of liquid deposited on any predetermined area of the agar surface is known or can be determined, the bacterial concentration may be calculated by counting the bacterial colonies within this known area and dividing by the volume thus giving the concentration. The unknown plate may also be compared to a standard set of plates by visually matching the whole plate or any comparable portion of the plates.

The number of bacterial colonies may be electronically counted by shining a light, e.g., a lasar beam, through the plate and onto a photodiode, the change in transparency of the plate, as caused by the bacteria, registering on the photodiodes to activate a counting circuit. The light must track the Petri dish in a spiral so that each of the colonies in a predetermined area may be counted or alternatively, the area may be determined in which a predetermined count of colonies is present.

It is accordingly an object of the present invention to obviate the deficiencies of the prior art as indicated above. Another object of the present invention is the provision of a method and apparatus for plating and counting aerobic bacteria.

It is another object of the present invention to provide a method for determining the concentration of an unknown bacterial solution.

It is still another object of the present invention to determine the concentration of an unknown bacterial solution using only a single bacterial growth plate for the determination.

It is yet another object of the present invention to associate the number of colonies to volume by counting the colonies on a known area of the agar.

It is still another object of the present invention to associate the number of colonies to volume by determining the area of the agar on which a predetermined number of colonies are counted.

Still another object of the present invention is the provision of a means for counting bacterial colonies using a light and a sensor having a photodiode and for relaying the number of bacterial colonies counted to the area on which they were deposited.

Still another object of the present invention is the provision of a means for counting aerobic bacteria which is fast, accurate and minimizes human error in its operation.

Other objects and many of the attendent advantages of the present invention will be readily appreciated as the same becomes better understood by reference to the following detailed description of an embodiment when considered in connection with the accompanying drawings in which like reference numerals designate like parts throughout the figures thereof.

BRIEF DESCRIPTION OF THE DRAWING

FIG. 4 is a partly schematic view of a side elevation of another embodiment of the present invention in which the bacteria is counted by means of a laser beam which beam moves in a spiral to scan a stationary agar plate;

FIG. 5 is a partly schematic rear elevation of the embodiment shown in FIG. 4; and FIG. 6 is a block diagram of the scan control and logic electronics for the embodiment of FIG. 4.

DESCRIPTION OF PREFERRED EMBODIMENTS

Figure 1:
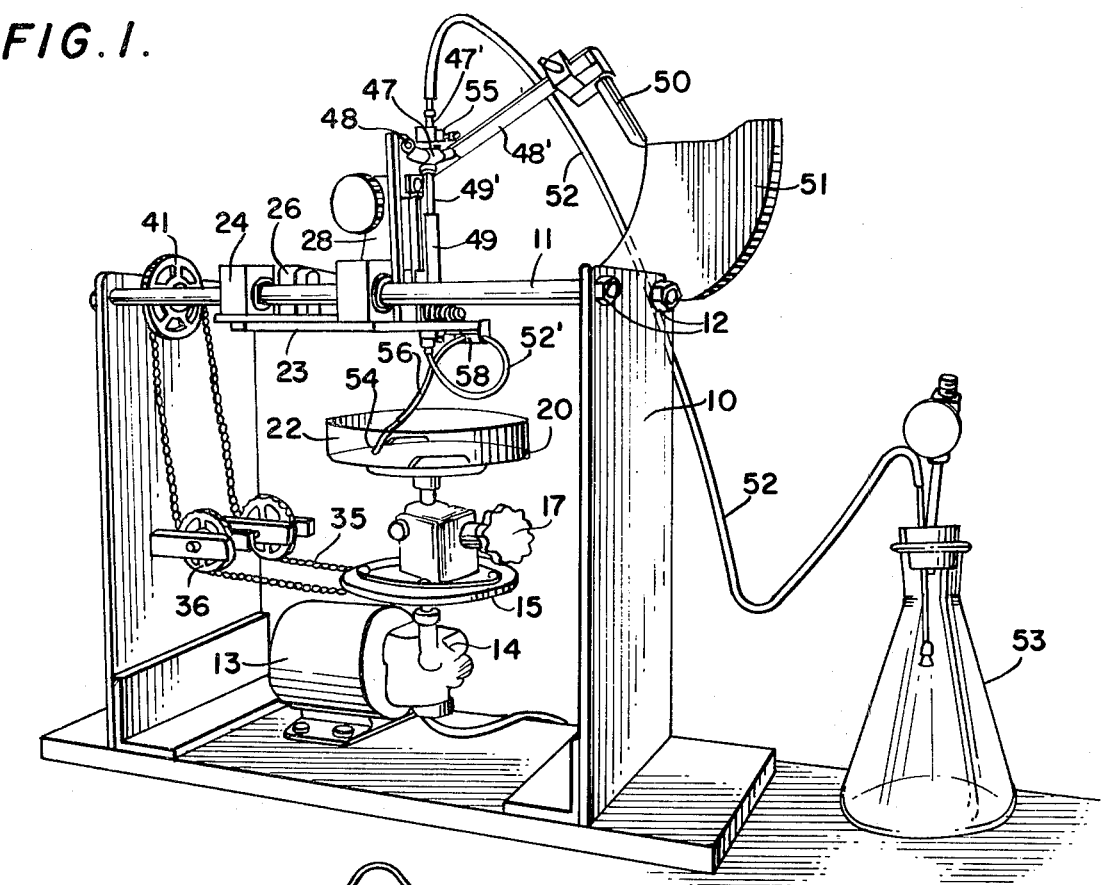
FIG. 1 shows a perspective view of a device used for depositing solution on an agar plate.
Figure 2:
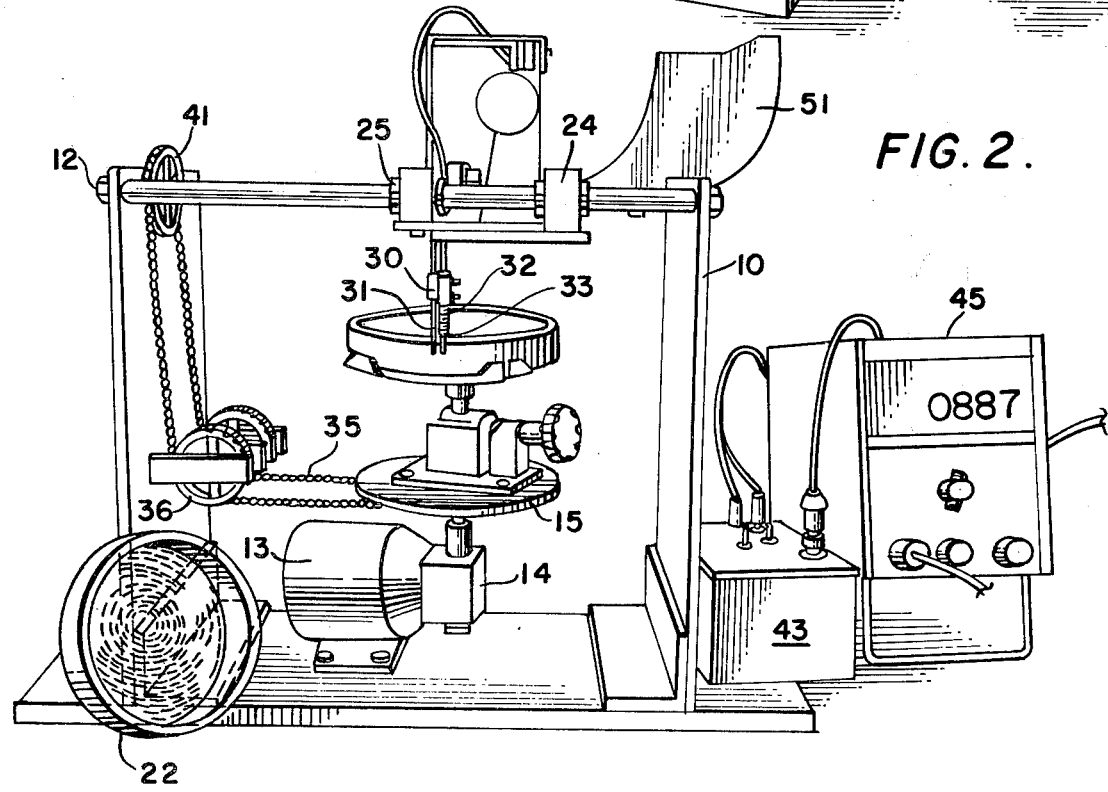
FIG. 2 shows a front elevation of a device used for counting bacteria by reflected light.
Figure 3:
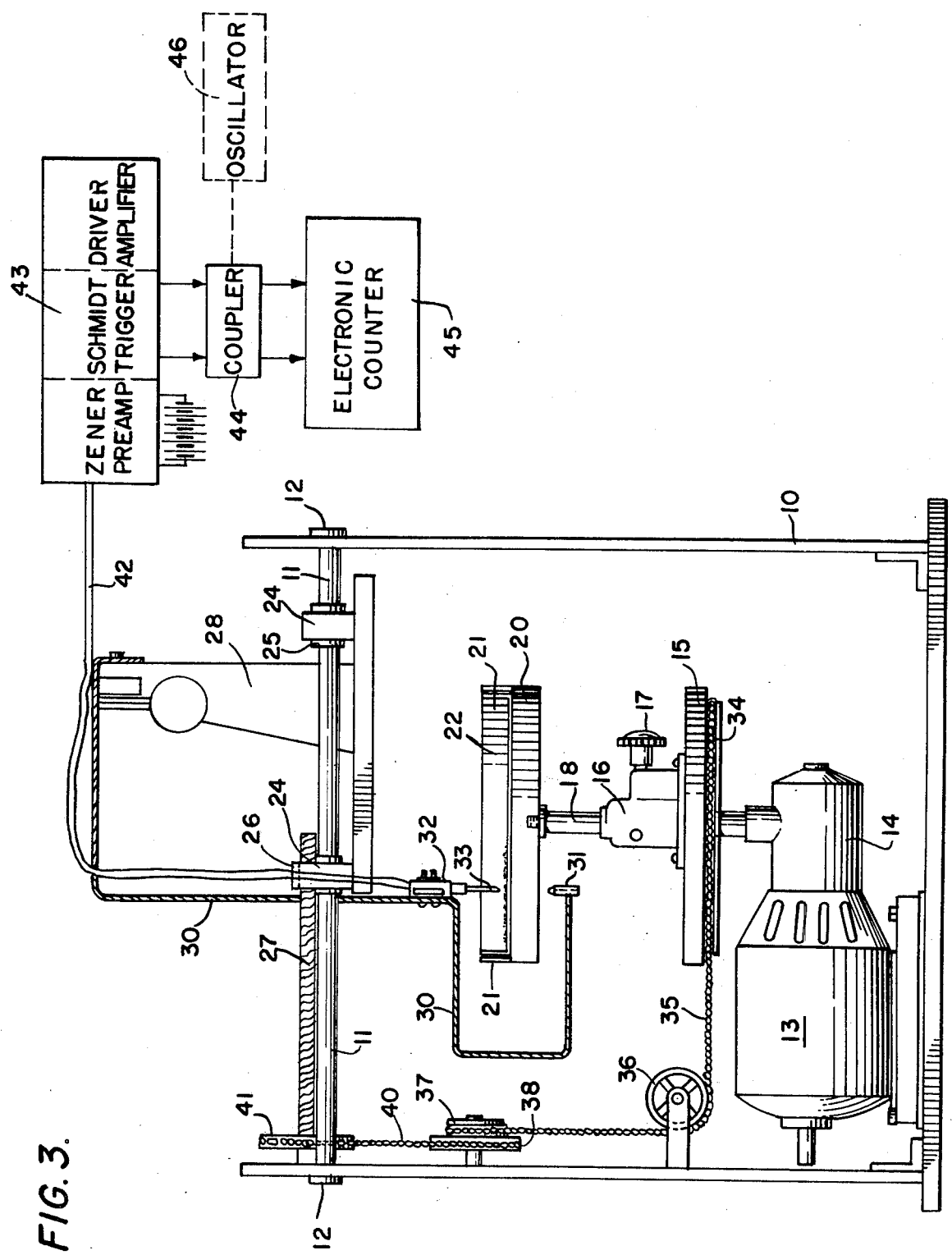
FIG. 3 is a partly schematic view of the present invention showing another device for counting bacteria by transmitted light and showing in greater detail the arrangement of the various components.

Referring now to FIGS. 1 to 3, there is shown a frame 10 which is substantially U-shaped and which rests on its horizontal parts with its legs extending vertically. Joining the two vertical legs near their upper ends is at least one horizontal crossbar 11, the bar being held in place in the vertical legs by end caps or nuts 12. Bolted to the bottom of the frame 10 is an electric motor 13, the end of the motor 13 having attached thereto a gearbox 14 which is used to rotate a disc 15. The disc 15 may be made of some light-weight metal such as aluminum and is mounted above gearbox 14 so that it is positioned horizontally and rotates about a vertical axis incorporated in the gearbox.

Bolted to the disc 15 so as to be integral and rotate with it is a height adjusting means 16, this means having an adjusting knob 17 which turns a rack and pinion or equivalent arrangement (not shown) to move a plunger up and down. Screwed to the end of plunger 18 is a disc 20, preferably of a transparent plastic also positioned in a horizontal plane and movable vertically when the plunger 18 is moved. The transparent plastic disc 20 has positioning studs 21 around its periphery, of a depth to hold a Petri dish 22, so that the dish will be centered when disc 20 rotates, even though this rotation will not be at a high rate.

Suspended from the crossbar 11 is moving platform 23 having an end bracket 24 at each of its ends for support. End brackets 24 have a transverse hole drilled therethrough of sufficient size to accommodate the crossbar 11 and linear ball bearings 25 within each crossbar 24 provide a sliding fit so that moving platform 23 can freely move along the crossbars. Also forming a part of the left bracket 24 there is a fixed half-nut 26, this half-nut encircling and cooperating with a lead screw 27 in the usual manner to move the platform 23 when the lead screw is turned. The opposite end of lead screw 27 from half-nut 26 is rotatably mounted in the vertical leg of frame 10.

Forming a part of, and integrally mounted on, the moving platform 23 there is a rack and pinion 28 which may serve as a holder for the hereafter described syringe used in applying solution to Petri dish 22 as will become apparent hereinafter.

In the embodiments of an apparatus for electronically counting the bacteria shown in FIGS. 2 and 3, which are modifications of the apparatus for plating the bacteria shown in FIG. 1, a bracket 30 is provided for furnishing support to light source 31 and to an electronic sensor 32. In the construction of FIG. 3, a portion of metal bracket 30 is C-shaped so that it extends on either side of the transparent disc 20, the light source 31 being on one end of the C, and below disc 20, while the other leg of the C holds the sensor 32 above the disc 20. It is obvious through this arrangement that light from source 31 shines through disc 20 and onto the phototube 33, the presence or absence of light striking the photodiode indicating the absence or presence of a bacterial colony on Petri dish 22. In some instances, where counting by reflected light is satisfactory, however, the light source may be above the disc 20 as shown in FIG. 2 in which case it is not necessary to provide a transparent disc and dish.

Immediately below, and fastened to, disc 15 there is a pulley 34 and a beaded chain 35 or the equivalent, the chain 35 passing around a smaller pulley 37 (FIG. 3) or directly to a larger pulley 41 (FIGS. 1 and 2). If desired integral with pulley 37 there may be provided a slightly larger pulley 38 so that when these two pulleys turn, a speed ratio output is obtained as shown in FIG. 3. In this embodiment, a second beaded chain 40 links a pulley 38 with the larger pulley 41, the latter pulley 41 being attached to lead screw 27 to serve as a means for rotating the lead screw.

Wires 42 carry a signal generated by a sensor 32 or a driving means 43 as shown in block form, which may be of any familiar configuration, such as, for example, a Zener preamplifier, a Schmidt trigger, and driver amplifier. The output of driving means 43 is connected to a coupler 44, and thence to an electronic counter 45, which may be any of the the devices well-known in the art. Should it be desirable, an oscillator 46 may be switched into the circuitry to enter a standard rate of counts (about 1,000Hz/sec) into the electronic counter when the photodiode is conducting. Micro-switches are preferably used to both stop the signal to the electronic counter and the motor when the sensor approaches the center of the Petri dish; these are preferably provided on the horizontal crossbars 11.

The function of the above-described circuitry is to count the number of bacteria appearing on portions of the dish. When the light is interrupted by the appearance of a bacterial colony, the counter will advance 1 digit. In one mode of operation, when the preselected number of colonies is counted, the electronics and the motor are inactivated at the place where the last colony was counted. The area of the portion of the plate traversed during the counting can then be visually or automatically determined and, knowing the amount of solution deposited in that area, the concentration of the sample solution can be calculated. Alternatively, the micro-switches may be used to stop the counting after a predetermined area has been traversed, thus allowing the same calculation to be made.

Referring now to FIG. 1, the invention is shown as it would be modified slightly to accomplish plating of an agar or other nutrient plate (Petri dish) with solution in a spiral configuration. The components bear the same part numbers as previously described with the exception that there is provided a coating device instead of a sensing apparatus.

A syringe 49 is mounted on the platform 23, while a hollow syringe plunger 49' is contained therein for vertical movement, the plunger 49' being connected to a rack and pinion device 48 including an arm 48', which device 48 is in turn carried on the mounting post 28 for vertical movement in a dove-tail-like groove in the mounting post 28. A valve 47 is mounted at the top of the plunger 49' on the device 48. On the end of the arm 48 there is a pointer 40 which rides along the contoured surface of a cam 51, the purpose of which is to control the movement of the plunger 48', in the syringe 49. A plastic tube 52 joins a vacuum flask 53 and valve arrangement 47 for connecting the tube 52 to a source of vacuum through the vacuum flask 53.

A second tube 52' passes from the bottom of the syringe 49 and then through a rigid support tube 56 from which it extends terminating in a tip 54 which rides on the agar plate 23. The rigid support tube 56 is supported in turn by a substantially horizontal pivot 58 which is preferably parallel to the crossbars 11. The weight of tube 56 pivotable about pivot 58 maintains the tip 54 against the agar plate 22. In this manner the tip 54 will ride on the surface of the agar despite any irregularities thereon. A cutoff 55 is furnished to control the valve 47 and seal off any application of vacuum from passing through the plunger 49' and the tube 52'.

The view given in FIG. 2 shows how agar plate 22 looks after the solution has been deposited on it. Also shown is another embodiment of electronic counter 45 with its driver 43.

FIGS. 4 and 5 show an alternative embodiment of an apparatus for counting the colonies on the agar plate prepared according to the method of the present invention. Instead of physically moving the light source and the agar plate in order that the light source spirally cover the agar plate, in the embodiment of FIGS. 4 and 5 the light source and the agar plate are held stationary while a system of mirrors is moved in order to cause the beam of light to travel in a spiral over the plate.

Referring now to FIGS. 4 and 5, the optical system of a laser beam counter is enclosed in a case 66 having a support plate 68 disposed therewithin. A laser 70, such as a helium neon laser, directs a beam of high intensity light through lens 72 which is then reflected by mirror 74 through lens 76. The light beam is then reflected by mirrors 77 and 79 mounted on x- and y-galvanometers 78 and 80 onto mirror 82 in a manner which will be discussed more fully hereinbelow. After reflecting from mirror 82 the light beam passes through agar plate 84, lens 86, diffuser plate 88 and lens 90 and is then directed by mirror 92 onto photodetector 94.

The path of the beam on fixed agar plate 84 is in the form of a decreasing Archimedes spiral which is generated by mirrors 77 and 79 attached to galvanometers 78 and 80. The sinusoidal signal to the galvanometers is 90° out of phase in order to generate a circle. The signal is controlled by a ramp generator which causes the circle to become smaller which is then an Archimedes spiral.

A block diagram of the scan drive and logic electronics with a laser beam counter of the present invention is shown in FIG. 6. All of the electronics shown therein are standard components in the state of the art and thus FIG. 6 is self-explanatory.

The x- and y-galvanometers 78 and 80 thus cause a laser beam of preselected diameter to scan in a spiral manner a spirally deposited plate 84 until a preselected number of colonies is counted or until a preselected area of that plate has been covered. The counter then displays the area that was necessary to obtain the preselected count or the count of colonies in the preselected area. This area is directly related to the sample volume deposited on the surface of the plate. Thus the number of colonies divided by the volume gives concentration or the number of bacteria per unit volume. If the preset number of colonies is not on the plate then the number of colonies counted on the total plate area is displayed.

As disclosed hereinabove a preset number of counts may be set and the area counter will display the area covered by the laser beam in which the preset number of colonies appear. Alternatively, the colony counter can display the number of colonies counted after a preset area has been covered. Unique features of this colony counter, therefore, are (1) the use of a preset number of counts to inactivate further counting of colonies and the counter's ability to produce positional data relating to where the beam finished counting; (2) the generation of an Archimedes spiral with a light beam for counting colonies; and (3) the use of a laser beam to count colonies.

Turning now to the operation of the entire system, first referring to FIG. 1, the electric motor 13, bolted to a U-shaped frame 10, operates the gearbox 14 to turn a disc 15 at a predetermined rotary speed. Atop the height adjusting means means 16 and turning with it is the transparent disc 20 which holds a Petri dish or agar plate 22, the plate also being rotated by the motor. The moving platform 23 moves across the frame 10 along the crossbars 11 under the influence of the lead screw 27 and half-nut 26, the platform being driven by motor 13, beaded chain 35, pulleys 37 and 38, beaded chain 40 and pulley 41 fastened to the lead screw. From this structure it is obvious that the platform moves over the agar plate at a speed which bears a definite and predetermined relation to the rate of rotation given to the plate. Mounting post 28, secured to platform 23, has the extended arm 48' attached to it, so that as the platform moves, pointer 50 follows along the face of cam 51 and operates to depress the plunger 49' of the syringe 49 as the platform moves over the agar plate. The syringe 49 dispenses fluid at a rate determined by the configuration of the cam 51 to the surface of the agar plate through the tip 54 of the plastic tube 52', positioned on the plate, tip 54 functioning as a moving stylus.

The plunger 49' of the syringe 49 is hollow with a valve 47 mounted on the upper end so that when a vacuum is applied through the valve from tube 52, fluid may be introduced through tip 54 and tube 52' to backflow into the syringe. Such a syringe is known as a backfill syringe such as that manufactured by Hamilton Company, Inc. under No. 87300. A new sample is introduced through the plastic tube 52' in this manner with a minimum of contamination. When the syringe is filled, valve cutoff 55 is closed and the system is ready to dispense fluid on the agar plate. Since the movement of platform 23 bears a fixed relationship to the rotation of the agar plate 22, it is clear that fluid dispensed from tip 54 onto the plate follows the configuration of an Archimedes spiral, and since the plunger 49' of the syringe 49 is being depressed by arm 48 the amount of solution being deposited on the agar is continuously decreasing resulting in a higher concentration of bacteria per unit length at the center of the spiral and a decreasing concentration per unit length as the edge of the plate is approached. After coating with bacterial solution, the plate must be incubated for the bacterial colonies to become visible, the time necessary for this being dependent upon the bacterial species.

Since the amount of liquid deposited on the agar is known, the bacterial concentration may be calculated by counting the bacterial colonies along any line or any group of lines. The unknown plate may also be compared to a standard set of plates by visually matching the whole plate or any comparable portion of the plates. Bacterial sensitivity to antibiotics may be determined by applying bacterial solutions to a plate having various quantities of antibiotics.

The number of bacterial colonies may be counted electronically using the apparatus of FIGS. 2 or 3 and the apparatus of FIGS. 4 to 6. FIGS. 2 and 3 use a portable light source in conjunction with a miniature photoelectric cell and an electronic counter. In FIG. 3 a sensor 32 having a photodiode 33 in its tip is mounted on platform 23 so that it moves across the agar plate, light from source 31 shining through transparent disc 20 and the agar plate to impinge on the sensor. The movement of the sensor over a bacterial colony causes a change in the intensity of the light on the photodiode. This causes the photodiode to conduct and send a signal through driving means 43, coupler 44, and on to electronic counter 45. Two modes of counting may be recorded on counter 45:

1. the total number of individual signals generated by the sensor, and
2. the total length of time the sensor is conducting.

In FIGS. 4 to 6, instead of the light source and the photo-detector physically moving with respect to the surface of the agar plate, an optical system is used whereby the light source, detector plate and agar plate all remain stationary while a series of mirrors are manipulated to cause the beam of light to traverse the agar plate in a spiral manner. The colonies may be counted in a similar manner to that described hereinabove in FIGS. 2 and 3 or as shown by the logic in FIG. 6. The logic may include means to avoid counting the same colony in two separate revolutions. For example, means may be included in the logic whereby if its presence of a bacterial colony is registered at the same angular position of two or more successive revolutions, the counter will not count the second or subsequent revolution as another colony.

From the above description of the structure and operation of the invention it is clear that the device offers many improvements over the shortcomings and weaknesses of the prior art apparatus. It is obvious that the invention provides a method and apparatus for quickly, easily and accurately determining aerobic bacterial colonies with a minimum of contamination, the result being a finite number rather than one obtained by estimation and human error. The device is successfully used over a bacterial concentration range of at least 100 to $1 \times 10^7$ bacteria per milliliter.

Obviously many modifications and variations of the present invention are possible in light of the above teachings. It is therefore to be understood that within the scope of the invention may be included modifications and variations other than those specifically described. For example, means other than the lead screw 27 may be used to advance the platform 23 such as a gear and a movable rack.

What is claimed is:

1. An apparatus for counting aerobic bacteria on a bacterial growth plate on which bacterial solution has been deposited in the form of a spiral with a continuously varying rate of deposition along the spiral, comprising:
    means for directing a beam of light toward the plate;
    sensing means, directed towards said plate so as to receive transmitted or reflected light from said beam directing means, for sensing the presence or absence of a bacterial colony on said plate;
    traversing means for causing the point of intersection of the beam of light from said beam directing means and the plate to spirally traverse across the surface of the plate;
    counting means for counting the bacterial colonies sensed by said sensing means; and
    measuring means for measuring a parameter which is related to the area traversed by said point of intersection while said counting means is counting in such a manner as to allow, in combination with other preset parameters, the determination of said area.

2. An apparatus in accordance with claim 1 wherein said traversing means comprises:
    rotating means for rotating the plate at a constant rate, and;
    moving means for causing the beam of light to move radially across the moving plate.

3. An apparatus in accordance with claim 2 wherein said moving means moves the beam directing means and the sensing means simultaneously radially with respect to the plate.

4. An apparatus in accordance with claim 3 wherein said beam directing means and said sensing means are located on opposite sides of the plate and said sensing means senses transmitted light.

5. An apparatus in accordance with claim 3 wherein said beam directing means and said sensing means are located on the same side of the plate and said sensing means senses reflected light.

6. An apparatus in accordance with claim 1 wherein said traversing means comprises;
    mirror means for causing the beam of light from said beam directing means which is stationary to traverse the surface of the plate which is stationary in the form of a spiral and onto said sensing means which is stationary.

7. An apparatus in accordance with claim 1 wherein said beam directing means is a laser.

8. An apparatus in accordance with claim 1 wherein said measuring means comprises revolution counting means for counting the number of revolutions of said point of intersection during the time said counting means is counting.

9. An apparatus in accordance with claim 1 wherein said measuring means comprises oscillator means for counting the time increments passing while said counting means is counting.

10. An apparatus for counting aerobic bacteria on a bacterial growth plate on which bacterial solution has been deposited in the form of a spiral with a continuously varying rate of deposition along the spiral, comprising:

means for directing a beam of light toward the plate;
sensing means for receiving transmitted or reflected light from said beam directing means and for sensing the presence or absence of a bacterial colony on the plate;
traversing means for causing the point of intersection of the beam of light from said beam directing means and the plate to spirally traverse across the surface of the plate, said traversing means comprising mirror means for causing the beam of light from said beam directing means which is stationary to traverse the surfaces of the plate which is stationary in the form of a spiral and onto said sensing means which is stationary; and
counting and measuring means for counting and determining the concentration of the bacterial colonies sensed by said sensing means.

* * * * *